United States Patent
Matveeva et al.

(10) Patent No.: US 11,937,609 B2
(45) Date of Patent: Mar. 26, 2024

(54) PROCESS FOR IMPROVING FRESHNESS OF FLAT BREADS INVOLVING COMBINATION OF MALTOGENIC ALPHA AMYLASE VARIANTS

(71) Applicant: Novozymes A/S, Bagsvaerd (DK)

(72) Inventors: Irina Victorovna Matveeva, Moscow (RU); Umut Köroglu, Istanbul (TR); Henrik Lundkvist, Malmö (SE); Silvia Strachan, Röschenz (CH); Hasim Sinik, Istanbul (TR)

(73) Assignee: Novozymes A/S, Bagsvaerd (DK)

( * ) Notice: Subject to any disclaimer, the term of this patent is extended or adjusted under 35 U.S.C. 154(b) by 659 days.

(21) Appl. No.: 17/048,459

(22) PCT Filed: Apr. 11, 2019

(86) PCT No.: PCT/EP2019/059203
§ 371 (c)(1),
(2) Date: Oct. 16, 2020

(87) PCT Pub. No.: WO2019/201725
PCT Pub. Date: Oct. 24, 2019

(65) Prior Publication Data
US 2021/0084911 A1    Mar. 25, 2021

(30) Foreign Application Priority Data

Apr. 19, 2018 (EP) .................................... 18168187

(51) Int. Cl.
| | | |
|---|---|---|
| *A21D 8/04* | (2006.01) | |
| *A21D 10/00* | (2006.01) | |
| *A21D 13/41* | (2017.01) | |
| *A21D 13/42* | (2017.01) | |
| *A21D 13/43* | (2017.01) | |
| *A21D 15/00* | (2006.01) | |
| *C12N 9/26* | (2006.01) | |

(52) U.S. Cl.
CPC .......... *A21D 8/042* (2013.01); *A21D 10/002* (2013.01); *A21D 13/41* (2017.01); *A21D 13/42* (2017.01); *A21D 13/43* (2017.01); *A21D 15/00* (2013.01); *C12N 9/2414* (2013.01); *C12Y 302/01133* (2013.01)

(58) Field of Classification Search
None
See application file for complete search history.

(56) References Cited

U.S. PATENT DOCUMENTS

2016/0135472 A1* 5/2016 Bellido .................. A21D 8/042
426/549

FOREIGN PATENT DOCUMENTS

| | | | |
|---|---|---|---|
| GB | 2417184 A | 2/2006 | |
| WO | WO-9943794 A1 * | 9/1999 | ............... A21D 2/26 |
| WO | 2006032281 A2 | 3/2006 | |
| WO | 2008148845 A2 | 12/2008 | |
| WO | 2010124206 A1 | 10/2010 | |
| WO | 2014131861 A2 | 9/2014 | |
| WO | 2018010966 A1 | 1/2018 | |

* cited by examiner

*Primary Examiner* — Jenna A Watts
(74) *Attorney, Agent, or Firm* — Yoshimi D. Barron

(57) ABSTRACT

A method for improving the freshness of flat breads comprising a) adding to flour or to a dough comprising a flour, a first maltogenic alpha-amylase having at least 70% identity to SEQ ID NO: 1, and compared to SEQ ID NO: 1 comprising the substitutions D261G, T288P, and F188L; and a second maltogenic alpha-amylase having at least 70% identity to SEQ ID NO: 1, and compared to SEQ ID NO: 1 comprising the substitutions D261G, T288P, F194Y, and N375S; and b) making flat breads from the dough.

17 Claims, No Drawings
Specification includes a Sequence Listing.

PROCESS FOR IMPROVING FRESHNESS OF FLAT BREADS INVOLVING COMBINATION OF MALTOGENIC ALPHA AMYLASE VARIANTS

REFERENCE TO A SEQUENCE LISTING

This application contains a Sequence Listing in computer readable form, which is incorporated herein by reference.

FIELD OF THE INVENTION

The present invention relates to a process for retarding the staling of flat breads, as well as flat breads obtainable by the method of the invention.

BACKGROUND OF THE INVENTION

Flat breads are the oldest and the most popular baking products in the world.

The producers are manufacturing extended types of flat bread such as pita, baladi, Lebanese, mafrood, shami, hapati, sangak, roti, tortillas, barbari, nan, taboon, shrak, mashrouh, nasir, tannoor, lavash, taftan, chapatti, pizza, tortillas, etc.

One of the crucial issues of flat breads for producers and consumers is the fast hardening, and thereby, the reduced quality of the flat bread which starts soon after baking.

In the bread-making industry, it is known to add bread-improving and/or dough-improving additives to the bread dough to improve texture, volume, flavor, freshness of the bread, as well as improving machinability of the dough.

GB 2417184 describes a process for preparation of wheat tortilla comprising using an exo-amylase and an emulsifier.

WO 2010/124206 describes the use of raw starch degrading enzymes to retard staling of flat breads.

However, many amylases require longer baking times to allow sufficient starch modification and are therefore less suitable to the rapid baking time of flat bread.

There is therefore still a need for finding improved enzyme solutions in flat bread production.

SUMMARY OF THE INVENTION

The present invention relates to a method for improving the freshness of flat breads so we claim:
A method for improving the freshness of flat breads comprising
  a) adding to flour or to a dough comprising a flour, a first maltogenic alpha-amylase having at least 70% identity to SEQ ID NO: 1, and compared to SEQ ID NO: 1 comprising the substitutions D261G, T288P, and F188L; and
  a second maltogenic alpha-amylase having at least 70% identity to SEQ ID NO: 1, and compared to SEQ ID NO: 1 comprising the substitutions D261G, T288P, F194Y, and N375S; and
  b) making flat breads from the dough.

In one embodiment, the flat breads are baked.

In one embodiment, the flour is selected from the group consisting of wheat flour, corn flour, rye flour, barley flour, oat flour, rice flour, sorghum flour, soy flour, flour from pulses like gram flour, and any combinations thereof.

In one embodiment, the flat breads are selected from the group consisting of pita, Arabic pita, baladi, Lebanese, mafrood, shami, hapati, sangak, roti, tortillas, barbari, nan, taboon, shrak, mashrouh, nasir, tannoor, lavash, taftan, chapatti, pizza, and any other flat bread having flat shape, large surface, and little crumb.

In one embodiment, the first maltogenic alpha-amylase has at least 75%, 80%, 85%, 90%, or 95% identity with SEQ ID NO:1.

In one embodiment, the second maltogenic alpha-amylase has at least 75%, 80%, 85%, 90%, or 95% identity with SEQ ID NO:1.

In one embodiment, the flat bread has a foldability at 2-7 days post baking which is better than the foldability of a flat bread which is prepared under the same conditions, but without treatment with the first and the second maltogenic alpha-amylase.

In one embodiment, the flat bread has eating properties at 2-7 days post baking which are better than the eating properties of a flat bread which is prepared under the same conditions, but without treatment with the first and the second maltogenic alpha-amylase.

In one embodiment, the flat bread has a softness at 2-7 days post baking which is better than the softness of a flat bread which is prepared under the same conditions, but without treatment with the first and the second maltogenic alpha-amylase.

In one embodiment, the dough further comprises one or more enzymes selected from the group consisting of aminopeptidase, amylase, alpha-amylase, beta-amylase, carboxypeptidase, catalase, chitinase, cutinase, cyclodextrin glycosyltransferase, deoxyribonuclease, esterase, galactanase, glucan 1,4-alpha-maltotetrahydrolase, glucanase, alpha-galactosidase, beta-galactosidase, glucoamylase, alpha-glucosidase, beta-glucosidase, glycosyltransferase, haloperoxidase, invertase, laccase, lipase, mannanase, mannosidase, oxidase, pectinolytic enzymes, peptidoglutaminase, peroxidase, phospholipase, phytase, polyphenoloxidase, proteolytic enzyme, ribonuclease, transglutaminase, and xylanase.

In one embodiment, the first maltogenic alpha-amylase is added in an amount of 0.01-100 mg of enzyme protein per kg of flour.

In one embodiment, the second maltogenic alpha-amylase is added in an amount of 0.01-50 mg of enzyme protein per kg of flour.

In one embodiment, the amount of the first maltogenic alpha-amylase is higher than the amount of the second maltogenic alpha-amylase.

In one embodiment, sugar is additionally added to the dough.

In one embodiment, a flat bread is obtainable by a method of the present invention.

In one embodiment, a flat bread dough premix comprising a first maltogenic alpha-amylase having at least 70% identity to SEQ ID NO: 1, and compared to SEQ ID NO: 1 comprising the substitutions D261G, T288P, and F188L; and a second maltogenic alpha-amylase having at least 70% identity to SEQ ID NO:1, and compared to SEQ ID NO: 1 comprising the substitutions D261G, T288P, F194Y, and N375S, and flour.

DETAILED DESCRIPTION OF THE INVENTION

Definitions

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

Variant: The term "variant" means a polypeptide having maltogenic alpha-amylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding one or more amino acids adjacent to and immediately following the amino acid occupying a position.

Improved property: When the enzyme composition according to the invention is incorporated into a dough in effective amounts, one or more properties in the flat bread obtained from the dough are improved compared to a flat bread obtained from a dough in which the enzyme composition is not added.

The improved property may be determined by comparison of a dough and/or a baked product prepared with and without addition of the enzyme composition of the present invention in accordance with the methods as known in the art.

Organoleptic qualities may be evaluated using procedures well established in the baking industry, and may include, for example, the use of a panel of trained taste-testers.

Flat Bread and Flat Bread Dough Compositions

As used herein, "flat bread" means bread prepared from sheeted dough, and which typically has a thickness of about one millimeter to a few centimeters.

A flat bread may be made from a simple mixture of flour, water, salt, and optionally yeast and sugar. The flat bread is then thoroughly rolled or sheeted into flattened dough. Flat breads have a very quick baking time (typically from 5 sec. to 5 minutes).

The flat breads may be leavened or unleavened, so in one embodiment, the flat bread is unleavened, i.e., made without yeast, and in another embodiment, the flat bread is made with yeast.

The flat bread may include further optional ingredients, such as sugar, olive oil, sesame oil, shortenings, spices, garlic, curry powder, diced jalapeños, chili powder, pepper, vegetables, and the like.

Examples of flat breads include tortilla, pita, and Indian flat bread (IFB). Further non-limiting examples include baladi, lavash, Lebanese, mafrood, shami, hapati, sangak, roti, barbari, nan, taboon, shrak, mashrouh, nasir, tannoor, lavash, taftan, chapatti, and pizza.

In a particular embodiment, the flat bread product is a pita.

As used herein "flat bread dough" means any dough used to prepare a flat bread.

The dough used to prepare a flat bread product may be made from any suitable flour source, e.g., flour sourced from grains, such as, wheat flour, corn flour, rye flour, barley flour, oat flour, rice flour, or sorghum flour, potato flour, soy flour, flour from pulses and combinations thereof. The flat bread may be wheat or gluten free flat breads.

Any flat bread process may be used to prepare the flat bread. The process of preparing flat bread generally involves the sequential steps of dough making (with an optional proofing step), sheeting or dividing, shaping or rolling, and proofing the dough, which steps are well known in the art.

In addition to preparing fresh flat bread dough or flat bread products, the present invention is also directed to a method for preparing flat bread dough that can be stored, e.g., at room temperature or with refrigeration, prior to baking.

An example of a method for preparing a flat bread dough that can be stored prior to baking includes the steps of making a dough (with an optional proofing), sheeting or dividing, shaping or rolling, proofing, and storing the dough.

In addition to preparing fresh flat bread dough or flat bread products, the present invention is directed to a method for preparing a frozen flat bread dough. The dough is frozen after preparation of the dough comprising the enzyme combination of the present invention (i.e., prior to baking). A frozen flat bread dough may be advantageous for storage and/or distribution.

An example of a method for preparing a frozen flat bread dough includes the steps of making a dough (with an optional proofing), sheeting or dividing, shaping or rolling, proofing, and freezing the dough. The present invention is also directed to a frozen flat bread dough comprising the enzyme combination of the present invention.

Industrial Processes

The present invention is particularly useful for preparing flat bread dough and flat bread products in industrialized processes, that is, in which the dough used to prepare flat bread and/or flat bread products are prepared mechanically using automated or semi-automated equipment.

The present invention provides significant advantages in that flat bread can now be prepared using automated or semi-automated processes in which the flat bread is stored for distribution and consumer use more than 24 hours after preparation.

The process of preparing flat bread generally involves the sequential steps of dough making (with optional proofing step(s)), sheeting or dividing, shaping or rolling, and proofing, the dough, which steps are well known in the art. In an industrial flat bread production process according to the present invention, one or more of these steps is/are performed using automated or semi-automated equipment.

Enzymes

Maltogenic Alpha-Amylases

According to the present invention, a first maltogenic amylase is added to the dough wherein the first maltogenic alpha-amylase has at least 70% identity to SEQ ID NO: 1, and compared to SEQ ID NO: 1 comprises the substitutions D261G, T288P, and F188L.

The first maltogenic amylase is disclosed in WO 1999/043794.

Preferably, the first maltogenic alpha-amylase is an enzyme having at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 1. Preferably, the first maltogenic alpha-amylase is SEQ ID NO:1 with the substitutions D261G, T288P, and F188L.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

The first maltogenic alpha-amylase is added in an effective amount for retarding the staling of the baked product. The amount will typically be in the range of 0.01-100 mg of enzyme protein per kg of flour, e.g., 0.05-10 mg of enzyme protein per kg of flour; e.g., 0.1-10 mg of enzyme protein per kg of flour.

According to the present invention, additionally, a second maltogenic amylase is added to the dough, wherein the second maltogenic alpha-amylase has at least 70% identity to SEQ ID NO: 1, and compared to SEQ ID NO: 1 comprises the substitutions D261G, T288P, F194Y, and N375S.

The second maltogenic amylase is disclosed in WO 2008/148845.

Preferably, the second maltogenic alpha-amylase is an enzyme having at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 1. Preferably, the second maltogenic alpha-amylase is SEQ ID NO:1 with the substitutions D261G, T288P, F194Y, and N375S.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

The second maltogenic alpha-amylase is added in an effective amount for retarding the staling of the baked product. The amount will typically be in the range of 0.01-50 mg of enzyme protein per kg of flour, e.g., 0.05-10 mg of enzyme protein per kg of flour; e.g., 0.1-10 mg of enzyme protein per kg of flour.

According to the present invention, the amount of the first maltogenic alpha-amylase may be higher than the amount of the second maltogenic alpha-amylase in the flat bread dough.

Additional Enzymes

Optionally, one or more additional enzymes, such as aminopeptidase, amylase, alpha-amylase, beta-amylase, carboxypeptidase, catalase, chitinase, cutinase, cyclodextrin glycosyltransferase, deoxyribonuclease, esterase, galactanase, glucan 1,4-alpha-maltotetrahydrolase, glucanase, alpha-galactosidase, beta-galactosidase, glucoamylase, alpha-glucosidase, beta-glucosidase, glycosyltransferase, haloperoxidase, invertase, laccase, lipase, mannanase, mannosidase, oxidase, pectinolytic enzymes, peptidoglutaminase, peroxidase, phospholipase, phytase, polyphenoloxidase, proteolytic enzyme, ribonuclease, transglutaminase, and xylanase, may be used together with the enzyme composition according to the invention.

The additional enzyme(s) may be of any origin, including mammalian and plant, and preferably of microbial (bacterial, yeast or fungal) origin.

The glucoamylase for use in the present invention include glucoamylases having a sequence identity of at least 50%, at least 60%, at least 65%, at least 70%, at least 75%, at least 80%, at least 85%, at least 90%, at least 95%, at least 96%, at least 97%, at least 98%, or at least 99% to the amino acid sequence of the *A. niger* G1 or G2 glucoamylase (Boel et al. (1984), EMBO J. 3 (5), p. 1097-1102), the *A. awamori* glucoamylase disclosed in WO 84/02921, or the *A. oryzae* glucoamylase (Agric. Biol. Chem. (1991), 55 (4), p. 941-949). A suitable commercial glucoamylase is GoldCrust™ obtainable from Novozymes NS.

Suitable commercial alpha-amylase compositions include, e.g., BAKEZYME P 300 (available from DSM) and FUNGAMYL 2500 SG, FUNGAMYL 4000 BG, FUNGAMYL 800 L, FUNGAMYL ULTRA BG and FUNGAMYL ULTRA SG (available from Novozymes NS).

The glucose oxidase may be a fungal glucose oxidase, in particular an *Aspergillus niger* glucose oxidase (such as Gluzyme Mono™ 1000 BG, available from Novozymes NS).

The xylanase which may be of microbial origin, e.g., derived from a bacterium or fungus, such as a strain of *Aspergillus*, in particular of *A. aculeatus, A. niger, A. awamori*, or *A. tubigensis*, from a strain of *Trichoderma*, e.g. *T. reesei*, or from a strain of *Humicola*, e.g., *H. insolens*.

Suitable commercially available xylanase preparations for use in the present invention include PANZEA BG, PENTOPAN MONO BG and PENTOPAN 500 BG (available from Novozymes NS), GRINDAMYL POWERBAKE (available from Danisco), and BAKEZYME BXP 5000 and BAKEZYME BXP 5001 (available from DSM).

The protease may be from *Bacillus*, e.g., *B. amyloliquefaciens*.

The phospholipase may have phospholipase A1, A2, B, C, D or lysophospholipase activity; it may or may not have lipase activity. It may be of animal origin, e.g., from pancreas, snake venom or bee venom, or it may be of microbial origin, e.g., from filamentous fungi, yeast or bacteria, such as *Aspergillus* or *Fusarium*, e.g., *A. niger, A. oryzae* or *F. oxysporum*. A preferred lipase/phospholipase from *Fusarium oxysporum* is disclosed in WO 98/26057. Also, the variants described in WO 00/32758 may be used.

Suitable phospholipase compositions are LIPOPAN F, LIPOPAN XTRA, and LIPOPAN PRIME (available from Novozymes NS) or PANAMORE GOLDEN and PANAMORE SPRING (available from DSM).

Enzyme Treatment

The enzymes are added to the flat bread dough ingredients (i.e., prior to baking or freezing the dough), e.g., indirectly to the dough by adding it to the flour used to prepare the dough, or directly to the dough itself.

The enzymes may be added to flour or dough in any suitable form, such as, e.g., in the form of a liquid, in particular a stabilized liquid, or it may be added to flour or dough as a substantially dry powder or granulate. Granulates may be produced, e.g., as disclosed in U.S. Pat. Nos. 4,106,991 and 4,661,452. Liquid enzyme preparations may, for instance, be stabilized by adding a sugar or sugar alcohol or lactic acid according to established procedures. Other enzyme stabilizers are well-known in the art. The enzyme combination treatment may be added to the flat bread dough ingredients in any suitable manner, such as individual components (separate or sequential addition of the enzymes), or addition of the enzymes together in one step or one composition.

The dough may also comprise other conventional ingredients, e.g., one or more emulsifiers. Emulsifiers serve to improve dough extensibility and may also be of some value for the consistency of the resulting flat bread, as well as for its storage stability and handling. Examples of suitable emulsifiers are mono- or diglycerides, polyoxyethylene stearates, diacetyl tartaric acid esters of monoglycerides, sugar esters of fatty acids, propylene glycol esters of fatty acids, polyglycerol esters of fatty acids, lactic acid esters of monoglycerides, acetic acid esters of monoglycerides, lecithin or phospholipids, or ethoxylated monoglycerides. Particularly useful emulsifiers include monoglycerides, diacetyl tartaric acid esters of monoglyceride (DATEM) and sodium stearoyl lactylate (SSL).

Other conventional ingredients include proteins, such as milk powder, gluten, and soy; eggs (either whole eggs, egg yolks or egg whites); an oxidant such as ascorbic acid, potassium bromate, potassium iodate, azodicarbonamide (ADA), ammonium persulfate or potassium persulphate; an amino acid such as L-cysteine; a sugar such as sucrose, dextrose, etc.; a salt such as sodium chloride, calcium acetate, sodium sulfate or calcium sulfate, diluents such silica dioxide, starch of different origins. Still other convention ingredients include hydrocolloids such as CMC, guar gum, xanthan gum, locust bean gum, etc. Modified starches may be also used.

Pre-Mixes

It will often be advantageous to provide the enzymes used in the treatment of the present invention in admixture with other ingredients used to improve the properties of flat bread products. These are commonly known in the art as "premixes," which usually comprise flour.

Hence, in a further aspect, the present invention relates to a flat bread premix for improving the quality of dough used to prepare a flat bread product or flat bread products, which premix comprises a first maltogenic alpha-amylase having at least 70% identity to SEQ ID NO: 1, and compared to SEQ ID NO: 1 comprises the substitutions D261G, T288P, and F188L; and a second maltogenic alpha-amylase having at least 70% identity to SEQ ID NO: 1, and compared to SEQ ID NO: 1 comprises the substitutions D261G, T288P, F194Y, and N375S, and flour. Flour such as flour from grains, such as, wheat flour, corn flour, rye flour, barley flour, oat flour, rice flour, sorghum flour, soy flour, or flour from pulses like gram flour, and combinations thereof may be used.

In another embodiment, the present invention relates to a flat bread pre-mix comprising the enzyme combinations of the present invention and flour, such as, flour from grains, such as, wheat flour, corn flour, rye flour, barley flour, oat flour, rice flour, sorghum flour, and combinations thereof, and one or more additional enzymes, as previously described.

The pre-mix composition may be in liquid form or dry or substantially dry form.

Dough and Flat Bread Properties

In one embodiment, the flat bread prepared by the methods and compositions of the invention provides improved storage properties. The flat bread prepared by the methods and compositions of the present invention are used as anti-staling agents to improve the shelf life of the flat bread product. The anti-staling effect (and improved shelf life) of a flat bread product can be determined by a number of methods well known in the art.

Primarily anti-staling effectiveness is measured by the hardness (also referred to as "firmness" and the opposite of "softness") of the flat bread product. Hardness can be measured using a texture profile analyzer. Texture measurements for flat bread such as tortilla can be measured according to methods known in the art as disclosed in, e.g., Gomez-Mendez et al. "Instrumental and sensory techniques for the measurement of wheat tortilla texture." IFT Conference Paper, New Orleans (1996) and Mao, "Texture measurements of commercially available wheat flour tortillas." Poster presented at IFT Annual Meeting, Dallas, USA (Jun. 10-14, 2000).

Besides hardness/softness, stickiness, extensibility and elasticity are also important quality parameters for flat bread. Other important properties include rollability, foldability, flexibility, layering, bite and/or texture.

Other tests known in the art may be used to assess the shelf life and other organoleptic qualities of the flat bread prepared by the methods and compositions of the present invention.

Storage/Shelf Life

In one embodiment, the present invention relates to a flat bread having an improved shelf life at least 1 hour after baking. In one embodiment, the present invention relates to a flat bread having an improved shelf life at least 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours or 23 hours after baking. In one embodiment, the present invention relates to a flat bread having an improved shelf life at least 24 hours after baking. In another embodiment, the present invention relates to a flat bread having an improved shelf life at least 48 hours after baking. In another embodiment, the present invention relates to a flat bread having an improved shelf life at least 72 hours after baking. In another embodiment, the present invention relates to a flat bread having an improved shelf life at least 96 hours after baking. In another embodiment, the present invention relates to a flat bread having an improved shelf life at least 120 hours after baking.

In another embodiment, the present invention relates to a flat bread having an improved shelf life at least 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days or 21 days after baking.

Shelf life can be measured as follows: A flat bread is prepared using enzyme compositions of the present invention and compared to a control flat bread, that is, a flat bread prepared in the same way but without enzyme compositions of the present invention.

The flat bread may be stored in a sealed plastic bag at ambient temperature; e.g., at 25° C. After the storage period, (e.g., 1 hour, 24 hours, 48 hours, 72 hours, 96 hours, 7 days, 21 days etc.), the hardness of the flat bread may be measured using a texture analyser and compared to a control flat bread stored under identical conditions, or the flat bread may be evaluated by a trained baking panel. An improved shelf life may be defined as a flat bread which is less hard (i.e., softer) than the control as measured by the texture analyser or by the trained baking panel.

In addition to preparing fresh flat bread dough or flat bread products, the present invention is directed to a method for preparing flat bread dough that can be stored, e.g., at room temperature or with refrigeration, or frozen prior to baking. The dough can be stored and/or frozen after preparation of the dough and treatment by the enzyme combinations of the present invention (i.e., prior to baking) for 1 hour, 24 hours, 48 hours, 72 hours, 96 hours, 5 days, 6 days, 7 days, 8 days, 9 days, 10 days, 11 days, 12 days, 13 days, 14 days, 15 days, 16 days, 17 days, 18 days, 19 days, 20 days, 21 days, etc.

In one embodiment, the flat bread is also compared to a control in other quality parameters, such as, stickiness, extensibility, elasticity, rollability, foldability, flexibility, layering, bite and texture; especially foldability. The flat bread prepared by the enzyme treatment of the present invention is analyzed at a time after baking or during storage (e.g., 1 hour after baking and/or 24 hours, 48 hours, 72 hours, 96 hours, 7 days, 14 days, 21 days, etc. post baking).

The flat bread prepared by the enzyme treatment of the present invention preferably has improved qualities in terms of improved stickiness, extensibility, elasticity, rollability, flexibility, foldability, layering, bite and/or texture.

The flat bread may be prepared with other background enzymes.

The invention described and claimed herein is not to be limited in scope by the specific embodiments herein disclosed, since these embodiments are intended as illustrations of several aspects of the invention. Any equivalent embodiments are intended to be within the scope of this invention as well as combinations of one or more of the embodiments. Various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties. The present invention is further described by the following examples which should not be construed as limiting the scope of the invention. For example, routine modifications to optimize the methods of enzymatic modification according to the present invention are contemplated.

EXAMPLES

Example 1

Pita Breads—Evaluated after 2 Days of Storage

The pita breads were made using a straight dough recipe. The flour was wheat flour of moderate baking quality.

Enzymes Added:

First maltogenic alpha-amylase (SEQ ID NO:1 with the substitutions D261G, T288P, and F188L) in an amount of 1 mg enzyme protein per kg flour.

Second maltogenic alpha-amylase (SEQ ID NO: 1 with the substitutions D261G, T288P, F194Y, and N375S) in an amount of 1.6 mg enzyme protein per kg flour.

| Process: | min: |
|---|---|
| Mixing (spiral mixer) | 10 |
| Resting | 10 |
| Scaling (100 g) | 5 |
| Round & resting | 10 |
| Sheeting & resting | 10 |
| Baking (320° C.) | 2 |

The flat bread was stored in a sealed plastic bag at room temperature.

The results were evaluated in the following way:

TABLE 1

| External evaluation | Foldability/ Rollability | 1 Hard /Tough | 10 Easy to fold/ No breakage |
|---|---|---|---|
| | Appearance | 1 Blisters on surface/ uneven color | 10 Absence of blisters/Even color |
| | Layers separation | 1 Hard to separate | 10 Easy to separate |
| Eating properties | First bite | 1 Low/Firm | 10 High/Soft |
| | Freshness | 1 Low/Dry | 10 High/Moist |
| | Resilience | 1 Low/ Chewy, gummy | 10 High/ Resilient, short bite |

A trained panel was presented with two different pita breads and requested to do an evaluation with 1 as the lowest performance and 10 as the best performance. The pita breads were evaluated after 2 days of storage.

Results:

External Characteristics:

TABLE 2

| Pita characteristics | Control (no enzymes) | Enzyme blend according to the invention |
|---|---|---|
| Appearance | 3 | 9 |
| Foldability/rollability | 1 | 8 |
| Layer separation | 5 | 9 |

Eating Properties:

TABLE 3

| Pita characteristics | Control (no enzymes) | Enzyme blend according to Example 1 |
|---|---|---|
| First bite | 5 | 8 |
| Freshness | 5 | 8 |
| Resilience | 5 | 8 |
| Overall eating quality | 4 | 8 |

Conclusion:

The scores of first bite, freshness, resilience and eating qualities significantly exceeded the control.

Example 2

Pita Breads—Evaluated after 7 Days of Storage

The pita breads were made in industrial scale using a straight dough recipe (75 kg wheat flour, 2.3 kg fresh yeast, 0.9 kg salt, 3 kg sugar, 36 kg water, 0.2 kg sorbic acid).

The wheat flour was untreated flour.

Enzymes Added:

First maltogenic alpha-amylase (SEQ ID No:1 with the substitutions D261G, T288P, and F188L) in an amount of 4 mg enzyme protein per kg flour.

Second maltogenic alpha-amylase (SEQ ID NO: 1 with the substitutions D261G, T288P, F194Y, and N375S) in an amount of 0.4 mg enzyme protein per kg flour.

TABLE 4

| Process: | |
|---|---|
| Mixing with folk mixer, min | 14 |
| Temperature after mixing, °C. | 28 |
| Dividing into 90-92 g dough pieces, min | 2 |
| Resting, min | 15-25 |
| Sheeting to app. 1 mm thickness in two perpendicular directions, min | 1 |
| Fermentation, min | 12 |
| Baking at 400° C., sec | 30 |
| Cooling at ambient temperature, min | 25-30 |
| Packing in vacuum, min | 2 |

The flat breads were evaluated after 7 days by a trained panel with the following results:

TABLE 5

| Pita characteristics | Control (no enzymes) | Enzyme blend according to Example 2 |
|---|---|---|
| Appearance | 5 | 9 |
| Foldability/rollability | 5 | 9 |
| Softness | 5 | 8 |
| Chewiness | 5 | 8 |
| Overall eating properties | 5 | 7 |

Conclusion:

The scores of appearance, foldability/rollability, softness, and chewiness significantly exceeded the control.

Example 3

Lebanese Flat Bread—Evaluated after 3 Days of Storage

Lebanese flat bread was made in the following way:

TABLE 6

| Recipe of Lebanese bread | |
|---|---|
| Ingredients | Amounts, % (w/w) |
| White flour of 750 type | 100 |
| Fresh yeast | 2 |
| Salt | 0.25 |
| Sugar | 3 |
| Water | 52 |

Enzymes Added:

Mixture A: First maltogenic alpha-amylase (SEQ ID No:1 with the substitutions D261G, T288P, and F188L) in an amount of 4 mg enzyme protein per kg flour, and second maltogenic alpha-amylase (SEQ ID NO: 1 with the substitutions D261G, T288P, F194Y, and N375S) in an amount of 0.4 mg enzyme protein per kg flour Mixture B: Maltogenic alpha-amylase (SEQ ID No:1 with the substitutions D261G, T288P, and F188L) in an amount of 4.4 mg enzyme protein per kg flour Mixture C: Maltogenic alpha-amylase (SEQ ID NO: 1 with the substitutions D261G, T288P, F194Y, and N375S) in an amount of 4.4 mg enzyme protein per kg flour Procedure:

All the ingredients were mixed.

The dough was kept in a closed tank for fermentation for 30 min at ambient temperature.

The dough was divided into 100 g pieces.

The dough was flattened and baked in a tunnel oven for 10 sec. at 350° C.

The flat bread was cooled.

The flat bread was packed in plastic bag when the centre of the bread was 37° C.

Eating Properties

The eating properties of the bread were evaluated after 3 days of storage by a trained panel using the following 3 parameters:

First Bite:

Fold a slice of bread once and take a bite. Evaluate the force needed to make the first bite. The control sample is given 5. A higher force indicates firm bread and is given a lower rating. A low force indicates soft bread and is given a higher rating.

Bread Freshness:

Take a bite of the bread slice and evaluate the amount of saliva needed to chew the bread. The control sample is given 5. High amounts of saliva indicate a dry bread crumb and is given a lower rating. Low amounts of saliva indicate a moist bread crumb and is given a higher rating.

Chewiness:

Take a bite of the bread slice and count the number of chews needed until the bread is ready to be swallowed. The control sample is given 5. A large number of chews indicate low chewiness and is given a lower rating. A low number of chews indicates a high (better) chewiness and is given a higher rating.

TABLE 7

| | Evaluation after 3 days: | | | |
|---|---|---|---|---|
| Attributes | Control (=no enzymes) | Mixture A | Mixture B | Mixture C |
| Bread Freshness | 5 | 6.5 | 6 | 5.3 |
| Chewiness | 5 | 6 | 5.5 | 5 |
| First bite | 5 | 6.5 | 5.8 | 5.3 |
| Overall eating quality | 5 | 6.3 | 5.8 | 5.2 |

Conclusion:

The mixture of first maltogenic amylase (SEQ ID No:1 with the substitutions D261G, T288P, and F188L) in an amount of 4 mg enzyme protein per kg flour, and second maltogenic alpha-amylase (SEQ ID NO: 1 with the substitutions D261G, T288P, F194Y, and N375S) in an amount of 0.4 mg enzyme protein per kg flour, had better eating properties than Mixture B and had also better eating properties than Mixture C alone.

The invention claimed is:

1. A method for improving the freshness of flat breads comprising
   a) adding to flour or to a dough comprising a flour, a first maltogenic alpha-amylase having at least 95% identity to SEQ ID NO: 1, and compared to SEQ ID NO: 1 comprising the substitutions D261G, T288P, and F188L; and
   a second maltogenic alpha-amylase having at least 95% identity to SEQ ID NO: 1, and compared to SEQ ID NO: 1 comprising the substitutions D261G, T288P, F194Y, and N375S; and
   b) making flat breads from the dough, wherein the amount of the first maltogenic alpha-amylase is higher than the amount of the second maltogenic alpha-amylase per kg of flour.

2. The method according to claim 1, wherein the flat breads are baked.

3. The method according to claim 1, wherein the flour is selected from the group consisting of wheat flour, corn flour, rye flour, barley flour, oat flour, rice flour, sorghum flour, soy flour, flour from pulses, and any combination thereof.

4. The method according to claim 1, wherein the flat breads are selected from the group consisting of pita, Arabic pita, baladi, Lebanese, mafrood, shami, hapati, sangak, roti, tortillas, barbari, nan, taboon, shrak, mashrouh, nasir, tannoor, lavash, taftan, chapatti, and pizza.

5. The method according to claim 1, wherein the first maltogenic alpha-amylase has at least 99% identity with SEQ ID NO:1.

6. The method according to claim 1, wherein the second maltogenic alpha-amylase has at least 99% identity with SEQ ID NO:1.

7. The method according to claim 1, wherein the flat bread has a foldability at 2-7 days post baking which is improved when compared to the foldability of a flat bread which is prepared under the same conditions, but without the treatment with the first and the second maltogenic alpha-amylase.

8. The method according to claim 1, wherein the flat bread has eating properties at 2-7 days post baking which are improved when compared to the eating properties of a flat bread which is prepared under the same conditions, but without the treatment with the first and the second maltogenic alpha-amylase.

9. The method according to claim 1, wherein the flat bread has a softness at 2-7 days post baking which is improved when compared to the softness of a flat bread which is prepared under the same conditions, but without the treatment with the first and the second maltogenic alpha-amylase.

10. The method according to claim 1, wherein the dough further comprises one or more enzymes selected from the group consisting of aminopeptidase, amylase, alpha-amylase, beta-amylase, carboxypeptidase, catalase, chitinase, cutinase, cyclodextrin glycosyltransferase, deoxyribonuclease, esterase, galactanase, glucan 1,4-alpha-maltotetrahydrolase, glucanase, alpha-galactosidase, beta-galactosidase, glucoamylase, alpha-glucosidase, beta-glucosidase, glycosyltransferase, haloperoxidase, invertase, laccase, lipase, mannanase, mannosidase, oxidase, pectinolytic enzymes, peptidoglutaminase, peroxidase, phospholipase, phytase, polyphenoloxidase, proteolytic enzyme, ribonuclease, transglutaminase, and xylanase.

11. The method according to claim 1, wherein the first maltogenic alpha-amylase is added in an amount of 0.01-100 mg of enzyme protein per kg of flour.

12. The method according to claim 1, wherein the second maltogenic alpha-amylase is added in an amount of 0.01-50 mg of enzyme protein per kg of flour.

13. The method according to claim 1, further comprising adding sugar to the dough.

14. A flat bread obtained from the method of claim 1.

15. A flat bread dough premix comprising a first maltogenic alpha-amylase having at least 95% identity to SEQ ID NO: 1, and compared to SEQ ID NO: 1 comprising the substitutions D261G, T288P, and F188L; and a second maltogenic alpha-amylase having at least 95% identity to SEQ ID NO: 1, and compared to SEQ ID NO: 1 comprising the substitutions D261G, T288P, F194Y, and N375S, and flour, wherein the amount of the first maltogenic alpha-amylase is higher than the amount of the second maltogenic alpha-amylase per kg of flour.

16. The method according to claim 1, wherein the first maltogenic alpha-amylase has at least 99% identity with SEQ ID NO:1.

17. The method according to claim 1, wherein the second maltogenic alpha-amylase has at least 99% identity with SEQ ID NO:1.

* * * * *

SEQUENCE LISTING

<160> NUMBER OF SEQ ID NOS: 1

<210> SEQ ID NO 1
<211> LENGTH: 686
<212> TYPE: PRT
<213> ORGANISM: Geobacillus stearothermophilus

<400> SEQUENCE: 1

```
Ser Ser Ser Ala Ser Val Lys Gly Asp Val Ile Tyr Gln Ile Ile Ile
1               5                   10                  15

Asp Arg Phe Tyr Asp Gly Asp Thr Thr Asn Asn Asn Pro Ala Lys Ser
            20                  25                  30

Tyr Gly Leu Tyr Asp Pro Thr Lys Ser Lys Trp Lys Met Tyr Trp Gly
        35                  40                  45

Gly Asp Leu Glu Gly Val Arg Gln Lys Leu Pro Tyr Leu Lys Gln Leu
    50                  55                  60

Gly Val Thr Thr Ile Trp Leu Ser Pro Val Leu Asp Asn Leu Asp Thr
65                  70                  75                  80

Leu Ala Gly Thr Asp Asn Thr Gly Tyr His Gly Tyr Trp Thr Arg Asp
                85                  90                  95

Phe Lys Gln Ile Glu Glu His Phe Gly Asn Trp Thr Thr Phe Asp Thr
            100                 105                 110

Leu Val Asn Asp Ala His Gln Asn Gly Ile Lys Val Ile Val Asp Phe
        115                 120                 125

Val Pro Asn His Ser Thr Pro Phe Lys Ala Asn Asp Ser Thr Phe Ala
    130                 135                 140

Glu Gly Gly Ala Leu Tyr Asn Asn Gly Thr Tyr Met Gly Asn Tyr Phe
145                 150                 155                 160

Asp Asp Ala Thr Lys Gly Tyr Phe His His Asn Gly Asp Ile Ser Asn
                165                 170                 175

Trp Asp Asp Arg Tyr Glu Ala Gln Trp Lys Asn Phe Thr Asp Pro Ala
            180                 185                 190

Gly Phe Ser Leu Ala Asp Leu Ser Gln Glu Asn Gly Thr Ile Ala Gln
        195                 200                 205

Tyr Leu Thr Asp Ala Ala Val Gln Leu Val Ala His Gly Ala Asp Gly
    210                 215                 220

Leu Arg Ile Asp Ala Val Lys His Phe Asn Ser Gly Phe Ser Lys Ser
225                 230                 235                 240

Leu Ala Asp Lys Leu Tyr Gln Lys Lys Asp Ile Phe Leu Val Gly Glu
                245                 250                 255

Trp Tyr Gly Asp Asp Pro Gly Thr Ala Asn His Leu Glu Lys Val Arg
            260                 265                 270

Tyr Ala Asn Asn Ser Gly Val Asn Val Leu Asp Phe Asp Leu Asn Thr
        275                 280                 285

Val Ile Arg Asn Val Phe Gly Thr Phe Thr Gln Thr Met Tyr Asp Leu
    290                 295                 300

Asn Asn Met Val Asn Gln Thr Gly Asn Glu Tyr Lys Tyr Lys Glu Asn
305                 310                 315                 320

Leu Ile Thr Phe Ile Asp Asn His Asp Met Ser Arg Phe Leu Ser Val
                325                 330                 335

Asn Ser Asn Lys Ala Asn Leu His Gln Ala Leu Ala Phe Ile Leu Thr
            340                 345                 350

Ser Arg Gly Thr Pro Ser Ile Tyr Tyr Gly Thr Glu Gln Tyr Met Ala
        355                 360                 365
```

-continued

```
Gly Gly Asn Asp Pro Tyr Asn Arg Gly Met Met Pro Ala Phe Asp Thr
    370                 375                 380
Thr Thr Thr Ala Phe Lys Glu Val Ser Thr Leu Ala Gly Leu Arg Arg
385                 390                 395                 400
Asn Asn Ala Ala Ile Gln Tyr Gly Thr Thr Thr Gln Arg Trp Ile Asn
            405                 410                 415
Asn Asp Val Tyr Ile Tyr Glu Arg Lys Phe Phe Asn Asp Val Val Leu
            420                 425                 430
Val Ala Ile Asn Arg Asn Thr Gln Ser Ser Tyr Ser Ile Ser Gly Leu
        435                 440                 445
Gln Thr Ala Leu Pro Asn Gly Ser Tyr Ala Asp Tyr Leu Ser Gly Leu
    450                 455                 460
Leu Gly Gly Asn Gly Ile Ser Val Ser Asn Gly Ser Val Ala Ser Phe
465                 470                 475                 480
Thr Leu Ala Pro Gly Ala Val Ser Val Trp Gln Tyr Ser Thr Ser Ala
                485                 490                 495
Ser Ala Pro Gln Ile Gly Ser Val Ala Pro Asn Met Gly Ile Pro Gly
            500                 505                 510
Asn Val Val Thr Ile Asp Gly Lys Gly Phe Gly Thr Thr Gln Gly Thr
            515                 520                 525
Val Thr Phe Gly Gly Val Thr Ala Thr Val Lys Ser Trp Thr Ser Asn
    530                 535                 540
Arg Ile Glu Val Tyr Val Pro Asn Met Ala Ala Gly Leu Thr Asp Val
545                 550                 555                 560
Lys Val Thr Ala Gly Gly Val Ser Ser Asn Leu Tyr Ser Tyr Asn Ile
                565                 570                 575
Leu Ser Gly Thr Gln Thr Ser Val Val Phe Thr Val Lys Ser Ala Pro
            580                 585                 590
Pro Thr Asn Leu Gly Asp Lys Ile Tyr Leu Thr Gly Asn Ile Pro Glu
        595                 600                 605
Leu Gly Asn Trp Ser Thr Asp Thr Ser Gly Ala Val Asn Asn Ala Gln
    610                 615                 620
Gly Pro Leu Leu Ala Pro Asn Tyr Pro Asp Trp Phe Tyr Val Phe Ser
625                 630                 635                 640
Val Pro Ala Gly Lys Thr Ile Gln Phe Lys Phe Phe Ile Lys Arg Ala
                645                 650                 655
Asp Gly Thr Ile Gln Trp Glu Asn Gly Ser Asn His Val Ala Thr Thr
            660                 665                 670
Pro Thr Gly Ala Thr Gly Asn Ile Thr Val Thr Trp Gln Asn
        675                 680                 685
```